(12) United States Patent
Mueller-Lierheim

(10) Patent No.: US 6,228,333 B1
(45) Date of Patent: May 8, 2001

(54) DEVICE FOR CATALYTICALLY DISSOLVING HYDROGEN PEROXIDE

(75) Inventor: Wolfgang G. K. Mueller-Lierheim, Munich (DE)

(73) Assignee: MDLE Medical Device Laboratories Europe GmbH, Memmingen (DE)

( * ) Notice: Subject to any disclaimer, the term of this patent is extended or adjusted under 35 U.S.C. 154(b) by 0 days.

(21) Appl. No.: 09/202,590

(22) PCT Filed: Jun. 3, 1997

(86) PCT No.: PCT/EP97/02863

§ 371 Date: Oct. 18, 1999

§ 102(e) Date: Oct. 18, 1999

(87) PCT Pub. No.: WO97/48423

PCT Pub. Date: Dec. 24, 1997

(30) Foreign Application Priority Data

Jun. 17, 1996 (DE) .............................. 196 24 095

(51) Int. Cl.[7] ....................................... A61L 9/00
(52) U.S. Cl. .............................. 422/300; 422/30; 422/40; 422/292; 514/839; 514/840
(58) Field of Search .................................. 422/30, 28, 40, 422/300, 292; 514/839, 840

(56) References Cited

U.S. PATENT DOCUMENTS

| | | | |
|---|---|---|---|
| 4,826,658 | * 5/1989 | Kay | 422/30 |
| 5,270,002 | * 12/1993 | Neff, II et al. | 422/30 |
| 5,275,784 | 1/1994 | Perlaky | 422/28 |
| 5,468,448 | * 11/1995 | Nicolson et al. | 422/30 |
| 5,650,126 | * 7/1997 | Taoda et al. | 422/122 |

FOREIGN PATENT DOCUMENTS

| | | |
|---|---|---|
| 3843746 | 7/1990 | (DE) . |
| 42 43 410 | 6/1994 | (DE) . |
| 195 22 950 | 1/1997 | (DE) . |
| 93/06870 | 4/1993 | (WO) . |

* cited by examiner

Primary Examiner—Krisanne Thornton
(74) Attorney, Agent, or Firm—Evenson, McKeown, Edwards & Lenahan, P.L.L.C.

(57) ABSTRACT

An apparatus for the catalytic decomposition of $H_2O_2$ in an aqueous solution which is a contact lens care agent, wherein the catalyst is formed by a shaped body which is roughened by sand blasting and which is coated by a platinum layer 1 which is produced by sputtering.

12 Claims, 1 Drawing Sheet

DEVICE FOR CATALYTICALLY DISSOLVING HYDROGEN PEROXIDE

The invention concerns an apparatus as set forth in the classifying portion of claim 1.

In an apparatus of that kind which is known from U.S. Pat. No. 5,275,784, it is known, for contact lens care, for catalytically active platinum metal to be deposited in the form of a layer, for example by sputtering, on a support of polymer material, for the purposes of hydrogen peroxide decomposition, in an aqueous care solution. Difficulties are encountered here in regard to adequate adhesion between the catalytically active platinum layer and the plastic support. Relatively large amounts of platinum are required for the deposit of the catalytic platinum layer.

It is known from German patent specification DE 24 25 714 B2 for contact lenses and in particular soft contact lenses to be sterilised by means of hydrogen peroxide in an aqueous, in particular 3% aqueous hydrogen peroxide solution. To remove residues of hydrogen peroxide, they are decomposed by means of a decomposition catalyst to water and oxygen. That decomposition operation can also be conducted in the treatment bath for the contact lens sterilisation and disinfecting treatment.

The catalyst has a catalytically inactive carrier material on which a catalytically active layer is disposed. In the known catalyst that layer is formed from electrolytically deposited platinum black.

It is also known from U.S. Pat. No. 5,306,352, after the sterilisation of contact lenses by means of hydrogen peroxide, for residues of the hydrogen peroxide to be decomposed by means of a suitable catalyst, the catalyst material being applied to a carrier or substrate of plastic material.

The object of the invention is to provide an apparatus of the kind set forth in the opening part of this specification with which improved adhesion between the platinum layer and supports is achieved.

In accordance with the invention that object is attained by the characterising portion of claim 1.

The platinum layer can be applied in the form of an extremely thin film to the preferably roughened surface of the shaped body of glass or the $TiO_xN_y$-support, the film preferably imitating the surface roughness. That not only provides for improved adhesion between the catalytically active platinum film and the support, but in addition a reduced amount of platinum metal is required in the layer-formation procedure. A sufficiently large catalytically active surface layer is produced on the shaped body with a small volume in respect of the shaped body or a reduced surface area in terms of the shaped body. A preferred thickness for the platinum layer is in the range of from 0.1 to 1 $g/m^2$.

The surface roughness is preferably produced by mechanical surface treatment, in particular by particle blasting. Preferably the blasting process is a sand blasting process for use in roughening the surface of the support. The shaped body can comprise a suitable material. Preferably however glass is used as the material for the shaped body. It has been found that a glass surface which is roughened by sand blasting affords excellent adhesion in relation to the platinum layer, in particular when it is applied by sputtering. An extremely thin layer can be produced by sputtering on the glass surface which is roughened by sand blasting.

That platinum layer which is produced by sputtering is obtained by a platinum target being bombarded with high-energy ions of an inert substance, for example argon, neon and the like, so that platinum is deposited in pure form as a platinum layer on the shaped body. The shaped body provided with $TiO_xN_y$ can comprise plastic material or another suitable carrier material such as ceramic and the like. The platinum layer which is deposited by sputtering has a high level of adhesion on the shaped body which is roughened in particular by sand blasting and can be formed as a thin film of uniform thickness. The uniform thin layer with a high degree of purity can be applied reproducibly in terms of its thickness in a controlled manner by suitable process control in the sputtering operation. In particular the size of the platinum layer may be such that it can be used upon use of the catalyst in an aqueous, in particular 3% hydrogen peroxide care system for contact lenses. The layer may be of such a nature that a sufficient sterilisation effect is achieved by the hydrogen peroxide on the contact lenses to be treated, in particular soft contact lenses, with subsequent decomposition of any residual hydrogen peroxide still present in the treatment solution.

The catalytically active apparatus may preferably be a component of a contact lens care system in which the contact lens is disposed in a container and the contact lens care and sterilisation procedure is effected in that container by means of aqueous care agent solution with a 3% hydrogen peroxide content. The platinum layer is adjusted in such a way that the hydrogen peroxide has a sufficient period of action for disinfecting the contact lenses to be treated in the container and that subsequently to the disinfecting treatment residual hydrogen peroxide is effectively broken down into the constituents water and oxygen.

The invention will be described in greater detail by means of embodiments with reference to the Figures in which.

Figure 3:
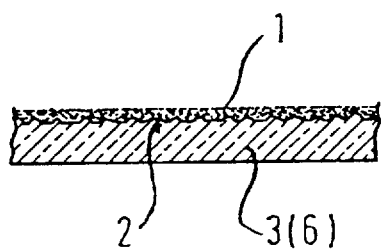

FIG. 3 diagrammatically shows a part of the catalytically active surface in the two embodiments.

Figure 1:
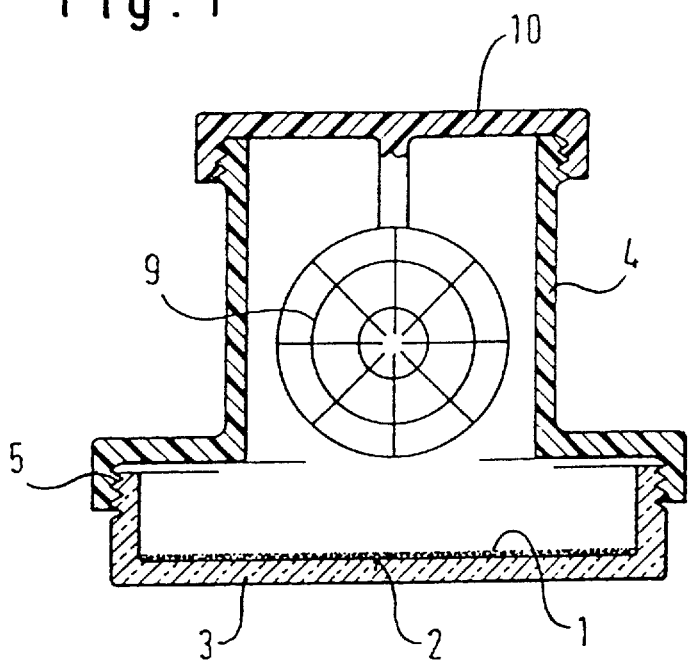
FIG. 1 shows a first embodiment.
Figure 2:
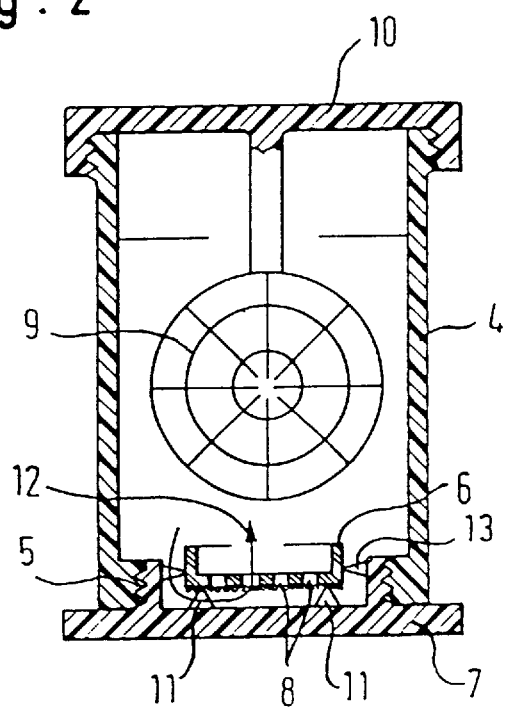
FIG. 2 shows a second embodiment.

The embodiments illustrated in FIGS. 1 and 2 are used in contact lens care and each have a container 4 which can be used as a storage or care container for contact lenses. The contact lenses to be treated are disposed in a basket 9 which can be pivoted open, as is known for example from U.S. Pat. No. 5,275,784. In the care procedure the contact lenses to be treated are immersed in the container 4 in an aqueous care agent solution which has a 3% hydrogen peroxide content. The basket 9 can be fixed to a cover 10 which can be screwed on to the container 4.

To close the bottom the embodiment of FIG. 1 has a bottom portion 3 which can be screwed by means of screwthread engagement 5 to the lower portion of the container 4. The embodiment shown in FIG. 2 also has a container bottom 7 which can be screwed on.

In the embodiment shown in FIG. 1 the container bottom or the screw-on bottom portion 3 preferably comprises glass. The bottom portion 3 forms the shaped body or the support for a catalytically active platinum layer 1 applied to the inside of the bottom portion 3. The surface which is covered with the platinum layer 1 has been previously roughened by a mechanical treatment process, in particular a blasting process, in which the surface was treated with particle blasting jets, in particular sand blasting jets, thus giving a roughened surface 2 on the glass material of the bottom portion 3. The configuration of the roughened surface 2 on the glass support (bottom portion 3) and the platinum layer applied thereto is diagrammatically shown in FIG. 3. As can be seen from FIG. 3 the platinum layer 1 which was preferably applied by sputtering adapts itself to the roughnesses of the surface and in relation to the glass support enjoys an elevated level of adhesion by virtue of the roughness of the surface which was preferably produced by a sand blasting treatment. In the embodiment of FIG. 1 substantially the entire bottom region, that is to say the inside surface of the bottom portion 3, is roughened and covered with the catalytically active platinum layer.

In the embodiment shown in FIG. 2 the screw-on container bottom 7 can comprise the same plastic material as the container 4. Provided on the container bottom 7 is an insert 6 in the form of a glass plate which is apertured or which has bores 8. The glass plate is preferably roughened at its underside as shown in FIG. 3 and provided with the platinum layer 1. It is however also possible for the top side to be roughened and provided with the platinum layer 1. The platinum layer is also applied in the same manner by sputtering in this embodiment. The underside of the apertured glass plate of the insert 6 is held at a given spacing from the container bottom 7 by spacers 11. That ensures that the oxygen produced upon catalytic decomposition rises in the form of oxygen bubbles and thus causes a circulatory effect so that hydrogen peroxide to be decomposed is circulated (arrow 12) and effectively decomposed. Lateral spacers 13 may also be provided in order to promote the circulatory effect.

What is claimed is:

1. Apparatus for catalytic decomposition of hydrogen peroxide in an aqueous solution, comprising a receiving container containing the aqueous solution, and a shaped body coated with a platinum layer acting as a catalyst and having a surface area which is in a direct contact with the hydrogen-peroxide containing aqueous solution, wherein the platinum layer is applied by sputtering on the shaped body which is comprised of glass, and wherein the platinum layer has a thickness in a range of from 0.1 to 1 $g/m^2$.

2. Apparatus according to claim 1 wherein the shaped body is roughened by mechanical surface treatment.

3. Apparatus according to claim 2, wherein the treatment is one of particle blasting and sand blasting.

4. Apparatus according to claim 1, wherein the platinum layer is applied to a roughened surface of the shaped body.

5. Apparatus according to claim 1, wherein the shaped body is releasably secured to a storage container.

6. Apparatus according to claim 5, wherein the shaped body forms a bottom portion of the storage container.

7. Apparatus according to claim 5, wherein the shaped body is secured to the storage container by a screw connection.

8. Apparatus according to claim 5, wherein the shaped body is in the form of an insert in the storage container.

9. Apparatus according to claim 8, wherein the insert has bores arranged at a predetermined spacing from a bottom of the container.

10. Apparatus according to claim 9, wherein the bores are provided in an insert portion which extends substantially parallel to the container bottom.

11. Apparatus according to claim 11, wherein the platinum layer is arranged in an aqueous contact lens care agent.

12. Apparatus according to claim 11, wherein the contact lens care agent is a 3% $H_2O_2$ solution for disinfecting contact lenses.

* * * * *